US011458332B2

(12) United States Patent
Isola (10) Patent No.: US 11,458,332 B2
(45) Date of Patent: Oct. 4, 2022

(54) OPTIMIZING FRACTIONATION SCHEMES IN RADIATION THERAPY USING BIOLOGICAL IMPACT CALCULATION

(71) Applicant: KONINKLIJKE PHILIPS N.V., Eindhoven (NL)

(72) Inventor: Alfonso Agatino Isola, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 16 days.

(21) Appl. No.: 16/979,801

(22) PCT Filed: Mar. 6, 2019

(86) PCT No.: PCT/EP2019/055485
§ 371 (c)(1),
(2) Date: Sep. 10, 2020

(87) PCT Pub. No.: WO2019/174979
PCT Pub. Date: Sep. 19, 2019

(65) Prior Publication Data
US 2021/0052916 A1    Feb. 25, 2021

(30) Foreign Application Priority Data
Mar. 13, 2018  (EP) .................................... 18161469

(51) Int. Cl.
*A61N 5/10* (2006.01)
(52) U.S. Cl.
CPC ......... *A61N 5/1031* (2013.01); *A61N 5/1038* (2013.01); *A61N 5/1048* (2013.01); *A61N 2005/1074* (2013.01)

(58) Field of Classification Search
CPC .............. A61N 5/103–1039; A61N 2005/1041
See application file for complete search history.

(56) References Cited

U.S. PATENT DOCUMENTS 8,222,616 B2    7/2012  Lu
9,764,162 B1    9/2017  Wllcut
(Continued)

FOREIGN PATENT DOCUMENTS

| GB | 2545018 A | 6/2017 |
| WO | 2010102068 A2 | 9/2010 |
| WO | 2017182300 A1 | 10/2017 |

OTHER PUBLICATIONS

International Search Report and Written Opinion of PCT/EP2019/055485, dated Jun. 4, 2019.
(Continued)

*Primary Examiner* — Thaddeus B Cox (57) ABSTRACT

A system and method for optimizing fractionation schemes in planning radiation therapy are provided, as well as a computer program and a computer program product for carrying out the method, and an arrangement for planning radiation therapy. For optimizing the fractionation schemes, the following steps are performed. Anatomical image data of a subject to be treated is received by a biological impact calculation module as well as a predetermined radiation therapy treatment plan comprising a dose distribution to be delivered to the subject. A first set of reference parameters of a fractionation scheme is received, and also a second set of parameters of a fractionation scheme is received. Based on this, the module calculates the biological impact of the radiation therapy treatment. The calculated biological impact results are provided simultaneously for the first and the second sets of received parameters.

15 Claims, 4 Drawing Sheets

(56) References Cited

U.S. PATENT DOCUMENTS

2008/0240351 A1* 10/2008 Bohsung .............. A61N 5/103
378/65
2010/0017226 A1    1/2010 Sundarapandian
2017/0157426 A1*  6/2017 Buchsbaum .......... A61N 5/1031
2019/0091488 A1*  3/2019 Ding .................... A61N 5/1043

OTHER PUBLICATIONS

Bortfeld, Thomas et al "Optimization of Radiation Therapy Fractionation Schedules in the Presence of Tumor Repopulation", Informs Journal on Computing, vol. 27, No. 4, 2015, pp. 788-803.

Uzan, J. et al "Radiobiologically Guided Optimisation of the Prescription Dose and Fractionation Scheme in Radiotherapy using BioSuite", The British Journal of Radiology, vol. 85, 2012, pp. 1279-1286.

Yasutaka, Sugano et al "Optimization of the Fractionated Irradiation Scheme considering Physical Doses to Tumor and Organ at Risk Based on Dose-Volume Histograms", Medical Physics, vol. 42, No. 11, 2015, pp. 6203-6210.

Vigneault, Eric et al "High-Dose-Rate Brachytherapy Boost for Prostate Cancer Treatment: Different Combinations of Hypfractionated Regimens and Clinical Outcomes", Radiotherpy and Oncology, vol. 124, 2017, pp. 49-55.

Emami, B. "Tolerance of Normal Tissue to Therapeutic Radiation" Reports of Radiotherapy and Oncology, vol. 1, No. 1, 2013.

Marks, Lawrence B. et al "Guest editor's introduction to QUANTEC: a users guide", Int. Journal Radiation Oncology Biology Physics, vol. 76, No. 3, 2010.

Fowler, John F. "The Linear-Quadratic formula and progress in fractionated radiotherapy: A review", British Journal of Radiology, vol. 62, 1989—Abstract Only.

Fowler, Jack F. "Biological factors influencing optimum fractionation in radiation therapy", ACTA Oncologica, vol. 40, 2001, pp. 712-717.

Fowler, Jack F, "The Radiobiology of prostate cancer including new aspects of fractionated radiotherpy", ACTA Oncologica, vol. 44, 2005, pp. 265-276.

Brenner, David J. et al "Direct evidence that prostate tumors show high sensitivity to fractionation (low $\alpha/\beta 2$ ratio) comparable to late-responding normal tissue", Int. J. Radiation Oncology Biology Physics, vol. 52, No. 1, 2002, pp. 6-13.

Lukka, Himu et al "A randomized trial comparing two fractionation schedules for patients with localized prostate cancer" Journal of Clinical Oncology, vol. 23, No. 25, 2005.

Fowler, J.F. "Is There an Optimum Overall Time for Head and Neck Radiotherapy? A Review, with New Modelling", Clinical Oncology, vol. 19, 2007, pp. 8-22.

Fowler, J.F. "Optimum Overall Times II: Extended Modelling for Head and Neck Radiotherapy", Clinical Oncology, vol. 20, No. 2, 2008, pp. 113-126.

Puck, Theodore T. et al "Action of x-rays on mammalian cells", Journal Exp. Medical, vol. 103, 1956, pp. 653-666.

* cited by examiner

OPTIMIZING FRACTIONATION SCHEMES IN RADIATION THERAPY USING BIOLOGICAL IMPACT CALCULATION

CROSS-REFERENCE TO PRIOR APPLICATIONS

This application is the U.S. National Phase application under 35 U.S.C. § 371 of International Application No. PCT/EP2019/055485, filed on Mar. 6, 2019, which claims the benefit of European Patent Application No. 18161469.4, filed on Mar. 13, 2018. These applications are hereby incorporated by reference herein.

FIELD OF THE INVENTION

The invention generally relates to the planning of fractionated radiation therapy. In particular the invention relates to determining fractionation schemes in radiation therapy. More specifically, the invention relates to the optimization of fractionation schemes in planning fractionated radiation therapy.

BACKGROUND OF THE INVENTION

In radiation therapy, target structures in patient's bodies, such as tumors are treated by subjecting them to radiation. The radiation can be in the form of external radiation such as photons, protons or particles, for example in external beam radiotherapy (EBRT) or internal radiation such as internal high dose rate (HDR) brachytherapy. The treatment is delivered in such a way that the radiation that is delivered to the target structures (TSs) is as high as possible, while at the same time the radiation delivered to the surrounding healthy tissue and structures, usually referred to as organs at risk (OARs), is as low as possible.

During the therapy, the dose of radiation is usually delivered to the patient over several radiation therapy sessions, with a recovery period between each session. This approach is known as fractionated radiation therapy, and the sessions are referred to as fractions. The reasoning behind this approach is that TS tumor tissue is expected to recover less well from a dose fraction than the healthy tissue including the OARs. In this way, by using a fractionation scheme, a larger total dose may be delivered to a patient.

Both the therapeutic necrotizing effect of the radiation on the TS and its negative impact on healthy OARs are affected by the fractionation scheme, i.e. the time schedule of dose delivery. This biological impact of fractionation generally depends on tissue type, and may also depend on the type of radiation used in the treatment. In order to compare different radiation treatments with different fractionation schemes, a qualitative effect model is needed to calculate the biological impact on the tissue. For this purpose, in scientific research, several models have been developed. The most widely used and accepted methods for investigating biological impact of fractionated radiation therapies are the Biologically Effective Dose (BED) model and the Linear-Quadratic (LQ) model.

A review is provided by J. F. Fowler in "The linear-quadratic formula and progress in fractionated radiotherapy", vol. 62, no. 740, August 1989, pages 679-694.

The treatment parameters for controlling a radiation therapy treatment are normally defined in a treatment plan, which is generated in a planning procedure on the basis of treatment goals specifying requirements for the radiation dose D delivered to be delivered to a TS. The requirements may also include a maximum value for the dose to be delivered to the OARs. Numerical optimization is used to determine the best total dose distribution to deliver. Usually this stage of the radiation therapy planning process is referred to as treatment planning or inverse planning.

In fractionated radiotherapy, in addition to determining the total delivered dose D, a choice also needs to be made as to how to divide the total dose over the delivery time. With this, the number of fractions N is also a planning parameter. N is chosen in a subsequent step in the radiation therapy planning process. Since tumor TSs and the healthy tissue including the OARs have generally different sensitivity to the dose delivered in a fraction and since they receive different dose distributions, the choice of N can have a differential biological impact on the TS verses the OARs. A well-chosen fractionation scheme could increase the desired therapeutic effect while limiting undesired damage to OARs. In current planning systems, typically only the delivered dose is calculated and optimized. The choice for the fractionation regime, and in particular the number N, is prescribed based on available clinical guidelines, historical precedence and the physician's judgement based on personal experience. In addition, there is a current trend to keep N as low as possible in view of treatment cost control. This means that in the current clinical practice the chosen fractionation scheme will often not be the optimal one.

SUMMARY OF THE INVENTION

The current invention recognizes that the fractionation scheme should not be a simple choice of the number of fractions, but should instead be considered as a second stage of the radiation therapy planning process. The current invention seeks to address need of the physician to be able to optimize fractionation schemes in planning radiation therapy based on the qualitative, biological impact of the fractionated radiotherapy treatment plan.

Thereto, a system and a method for optimizing fractionation schemes are provided, as well as a computer program and a computer program product for carrying out the method, and an arrangement for planning radiation therapy.

The system for optimizing fractionation schemes in planning radiation therapy of a subject comprises an input configured to receive anatomical image data of the subject and a predetermined radiation therapy treatment plan comprising a dose distribution to be delivered to the subject. The system further comprises an input configured to receive a first set of reference parameters of a fractionation scheme. The system further comprises a fractionation scheme input configured to receive a second set of parameters of a fractionation scheme, and the system comprises a biological impact calculation module comprising at least one qualitative effect calculation model, which calculation module is configured to calculate the biological impact of the radiation therapy treatment plan based on the anatomical image data of the subject, the dose distribution and a received set of parameters of a fractionation scheme. The system also comprises an output module configured to simultaneously provide at least two sets of results from the biological impact calculation module, wherein for the first set of results the reference parameters are used as the received set of parameters of the fractionation scheme and for the second set of results the second set of parameters are used as the received set of parameters of the fractionation scheme.

In an embodiment of the system, the output is further configured to provide a difference between the two sets of results. This allows for an improved comparison of the two sets of results when the biological impact for both is similar.

It is also an option for the output module to comprise a graphical display. This allows for visual comparison of the results. The fractionation scheme input may include a graphical interface. It is particularly advantageous when the output module and the fractionation scheme input are provided by the graphical unit interface. Such an embodiment, possibly in combination with any of the given options, is particularly user-friendly for the physician.

The method for optimizing fractionation schemes in planning radiation therapy of a subject comprises the steps of: receiving anatomical image data of the subject, receiving a predetermined radiation therapy treatment plan comprising a dose distribution to be delivered to the subject, receiving a first set of reference parameters of a fractionation scheme, receiving a second set of parameters of a fractionation scheme, calculating the biological impact of the radiation therapy treatment plan based on the anatomical image data, the dose distribution and both the first set and the second set of parameters of the fractionation scheme, and providing the calculated biological impact results simultaneously for the first and the second set of parameters. The method is preferably computer-implemented or implemented by other suitable calculation means. The results are preferably provided by displaying them on a display.

In a further embodiment of the method, the method steps are performed iteratively using different values for the second set of parameters in each iteration until an optimal set of parameters has been determined. In a particularly advantageous embodiment, this iteration is automated.

The arrangement for planning radiation therapy comprises an imaging device configured to provide an image of a subject to be treated, a contouring tool configured to provide anatomical image data based on the image provided by the imaging device, a system configured to determine a radiation therapy treatment plan comprising a dose distribution to be delivered to the subject, and the system for optimizing the fractionation scheme as described above.

An advantage of the current invention is that it makes use of a predetermined radiation therapy treatment plan comprising the dose distribution to be delivered to the subject. Because this total dose distribution is not calculated as part of the optimization of the fractionation scheme, calculation time is considerably reduced. This improves the speed of the optimization process of the fractionation scheme.

Another advantage lies in that the current invention displays in the biological impact of a fractionation scheme. This provides the physician with additional insight with regards to his parameter choice. This insight is provided for both the first, reference choice of parameters and for the second set of parameters.

A further advantage lies in the possibility to provide a second set of parameters of a fractionation scheme with simultaneous provision of the results from the biological impact calculations for both the first set of reference parameters as well as the second set of parameters. This allows the physician to compare the two options and make a choice as to which of the two is the fractionation scheme can best be used for treatment.

Another advantage lies in the option that the optimization of the fractionation scheme using the system and method may be automated. The second set of parameters may be varied iteratively and the resulting calculated biological impact optimized to find the maximum qualitative effect for the TS.

DETAILED DESCRIPTION OF THE INVENTION

Figure 1:
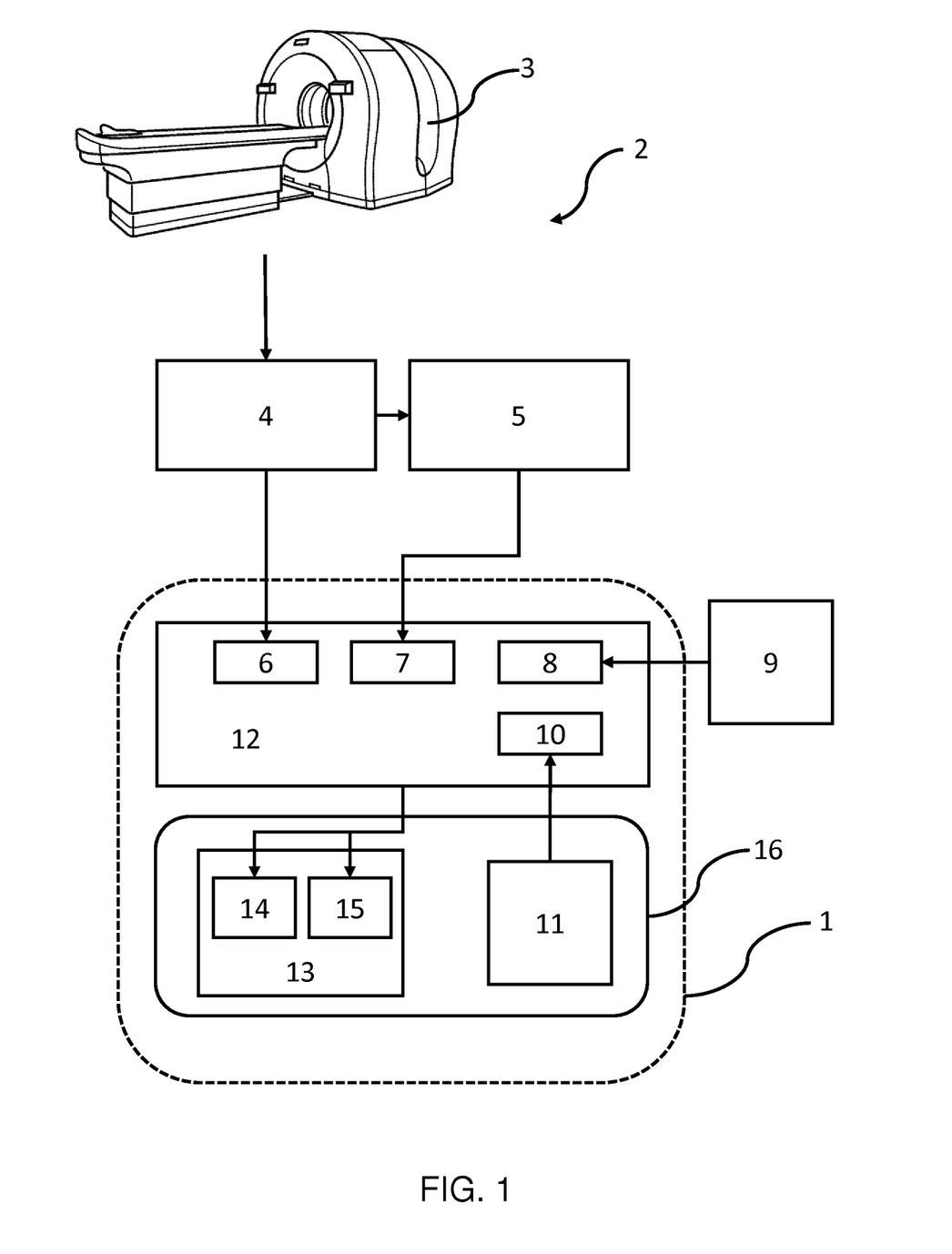
FIG. 1 schematically and exemplarily illustrates a system for optimizing fractionation schemes and further components of an arrangement for planning radiation therapy.

FIG. 1 illustrates a system 1 for optimizing fractionation schemes in planning radiation therapy of a subject. In this example, the system 1 is illustrated as part of an arrangement for planning radiation therapy 2.

In the arrangement for radiation therapy planning 2, a computed tomography (CT), magnetic resonance (MR), positron emission tomography (PET) or other medical image is acquired by an imaging device 3 and contoured using a contouring tool 4 to delineate the tumor TS and any neighboring OARs. The physician then selects various dose objectives, e.g. the dose to be delivered to the tumor TS along with constraints on radiation exposure to neighboring OARs.

Next treatment planning is performed, using a system configured to determine a radiation therapy treatment plan comprising a dose distribution to be delivered to the subject 5. During this planning a radiation therapy plan is developed comprising the dose to be delivered to the patient which achieves the dose objectives for the specific anatomy of the patient as represented by the CT or MR image and the anatomical image data such as the drawn tumor and OAR contours. The physician reviews the produced plan and makes final approval of the resulting calculated dose distribution.

When the dose distribution for the treatment plan has been approved, the fractionation scheme for the treatment needs to be determined. FIG. 1 shows a system 1 that may be used in optimizing the fractionation scheme.

The system has an input 6 configured to receive anatomical image data of the subject. This data can be contour data such as the contour data delineating the TSs and the OARs that has been determined earlier by the contouring tool 4. The system also has an input 7 configured to receive the predetermined radiation therapy plan comprising the dose distribution to be delivered to the subject. The system further has an input 8 configured to receive a first set of reference parameters of a fractionation scheme. In this example the set of reference parameters is selected from a reference parameter library 9. Alternatively, the parameters can be provided by a clinical workflow system or a different type of medical database. A further alternative is that the first set of reference parameters is entered into the input 8 by a physician based on his clinical experience or clinical guidelines. In the example of FIG. 1, the inputs 6, 7, 8 are illustrated as three separate units, but these may also be combined into two or even one unit.

In addition, the system also has a fractionation scheme input 10 configured to receive a second set of parameteres of a fractionation scheme. Also this second set of reference parameters may be selected from a reference parameter library or alternatively, may be provided by a clinical workflow system or a different type of medical database. In this example, the physician enters the second, alternative set of parameters to be compared to the reference parameters into the input through controls for entering the parameter values 11.

Based the information received through the inputs, a biological impact calculation module 12 now calculates the biological impact of the radiation therapy treatment. The calculations are based on at least one qualitative effect calculation model. The most widely used and accepted methods for investigating biological impact of fractionated radiation therapies are the Biologically Effective Dose (BED) model and the Linear-Quadratic (LQ) model. Qualititive effect models use tissue-specific parameters to characterize the tissue's radiation reaction. For example, the BED model uses an $\alpha/\beta$ ratio. The value for such parameters have been determined in clinical studies and a library of these values will be comprised in the calculation model as part of the qualitative effect calculation model. As an additional option, the calculation module may also be provided with multiple qualitative effect calculation models. The physicians can thus be presented with the option of choosing the preferred model.

The calculation module 12 calculates the biological impact of the radiation therapy treatment using the first set of reference parameters for the fractionation scheme to calculate the result as well as the second set of reference parameters that were received. An output module 13 simultaneously provides the sets of results. In the example of FIG. 1, the output module 13 is a display and the results are presented by displaying them as pictures 14, 15 side by side. Alternatively the results can also be displayed as graphs or data tables.

Because the results are provided simultaneously, the physician can compare the biological impact of the second fractionation scheme, for which in this example he has entered the parameters, with the biological impact of the reference scheme. He can then decide if one of the two options presents and optimal fractionation scheme for the radiation therapy or provide a different set of second parameters in the input 10 for further evaluation.

In the embodiment of FIG. 1, the output module 13 display and the data entry portion of the second parameter input 11 are combined in a graphical unit interface 16. Such a graphical unit interface 16 makes the system user-friendly for the physician. The graphical unit interface 16 and calculation module 12 may both be part of the same computational system such as a mainframe or personal computer, but the interface 16 can also be a separate device such as a wirelessly connected mobile device.

Figure 2:
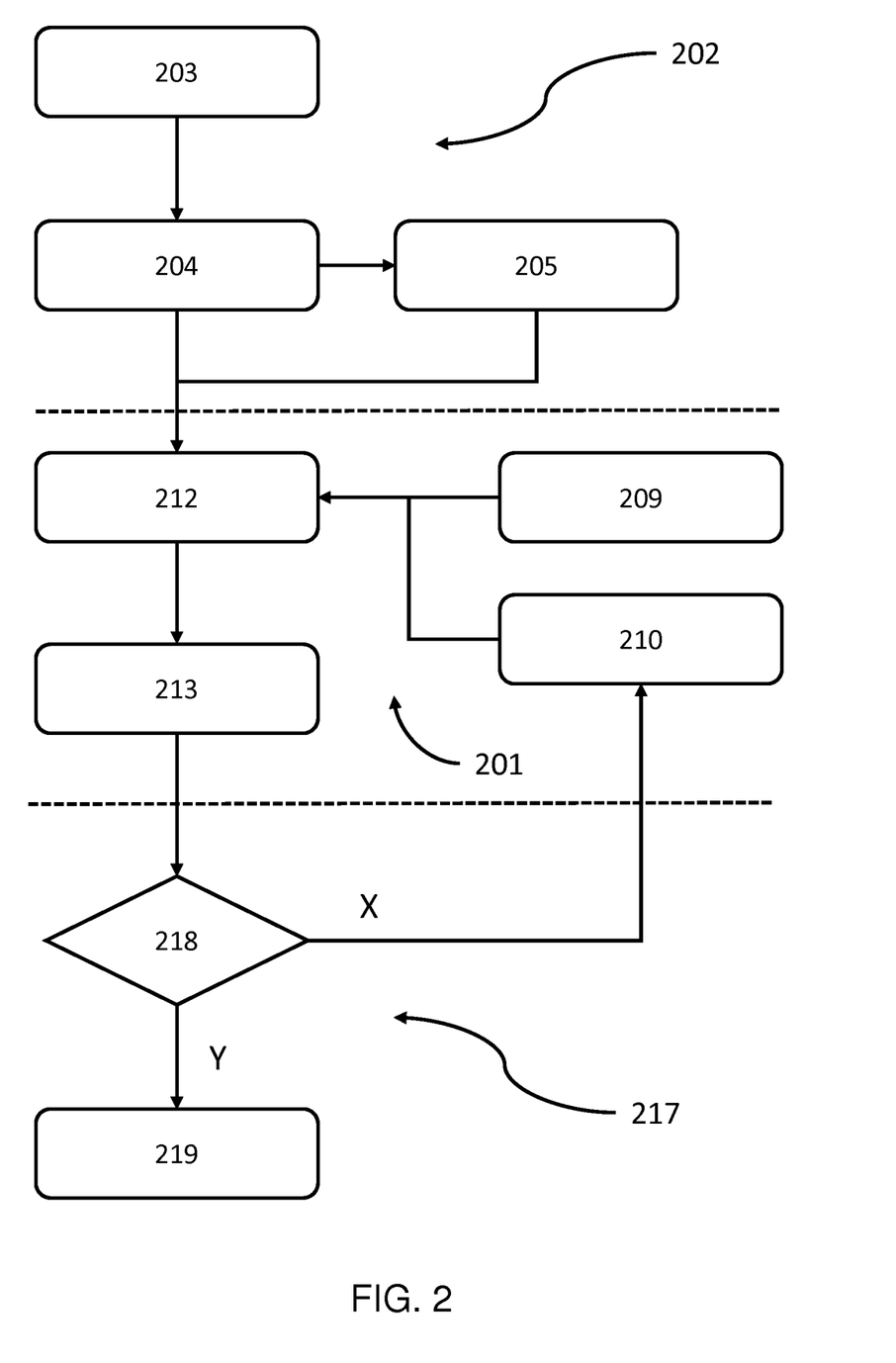
FIG. 2 schematically and exemplarily illustrates steps of a method for optimizing fractionation schemes in planning radiation therapy.

FIG. 2 schematically illustrates steps of a method for optimizing fractionation schemes in planning radiation therapy 201. The method is preferably computer-implemented or implemented by other suitable calculation means.

The method for optimizing the fractionation scheme 201 is preceded by radiation therapy planning steps 202 for determining a radiation therapy treatment plan comprising a dose distribution de be delivered to the subject. These method steps follow the same protocol as described in relation to the arrangement for planning radiation therapy 2 above. First a medical image of the patient is acquired 203. Then the anatomical image data of the subject to be treated is determined 204. Usually the anatomical image data is determined by contouring the medical image to delineate the TSs and any neighboring OARs. The physician then selects various dose objectives, e.g. the dose to be delivered to the tumor TS along with constraints on radiation exposure to neighboring OARs and treatment planning is performed 205. During this planning a radiation therapy plan is developed comprising the dose to be delivered to the patient which achieves the dose objectives for the specific anatomy of the patient as represented by the image data. The result is a predetermined radiation therapy plan.

These steps are followed by the method steps for optimizing the fractionation scheme 201 according to the invention. The anatomical image data of the subject to be treated, and the predetermined radiation therapy treatment plan comprising a dose distribution to be delivered to the subject are received as basis for caluting the biological impact of a fractionation scheme. Also and a first set of reference parameters of a fractionation scheme is received. This first set of references can be supplied 209 automatically by a data storage device or, alternatively, it can be entered by the physician. A second set of parameters of a fractionation scheme is also received 210. These parameters represent an alternative fractionation scheme to be compared to the first, reference fractionation scheme based on biological impact of both. This second set of parameters may also be supplied automatically by a data storage device or entered by the physician.

Based on this data, the biological inpact is calculated for both the first set and the second set of parameters of the fractionation scheme 212 and both sets of results are provided simultaneously 213. The data may for example be provided by displaying it. This can be done in graphical form, for example as a picture or a graph, or in numerical from, for example as a data table.

In an advantageous example 217, the method comprises the further step of comparing and evaluating the results 218. If one of the schemes can be accepted as the most suitable for delivery, the evaluation is positive Y, and the indicated fractionation scheme is established is the final, optimal plan 219. If neither of the schemes can be accepted as the most suitable for delivery, the evaluation is negative X. In this situation a further alternative set of second parameters is received and again the biological impact is calculated for the new parameters 212. The results are provided simultaneously with the reference results 213 and evaluated 218. In this way an iterative process is provided for optimizing the fractionation scheme. In the iterative process, the physician can enter the parameters and perform the evaluation in each iteration. Alternatively, the iterative process may be automated by using a predetermined variation for the second set of parameters and predetermined evaluation criteria. Preferably in the automated iterative process, an optimization algorithm is used.

Any of the method steps disclosed herein, may be recorded in the form of a computer program comprising instructions which when executed on a processor cause the processor to carry out such method steps. The instructions may be stored on a computer program product. The computer program product may be provided by dedicated hardware as well as hardware capable of executing software in association with appropriate software. When provided by a processor, the functions can be provided by a single dedicated processor, by a single shared processor, or by a plurality of individual processors, some of which can be shared. Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system, or apparatus or device, or a propagation medium. Examples of a computer-readable medium include a semiconductor or solid state memory, magnetic tape, a removable computer diskette, a random access memory "RAM", a read-only memory "ROM", a rigid magnetic disk and an optical disk. Current examples of optical disks include compact disk read only memory "CD-ROM", compact disk read/write "CD-R/W", Blu-Ray™ and DVD. Examples of a propagation medium are the Internet or other wired or wireless telecommunication systems.

Figure 3:
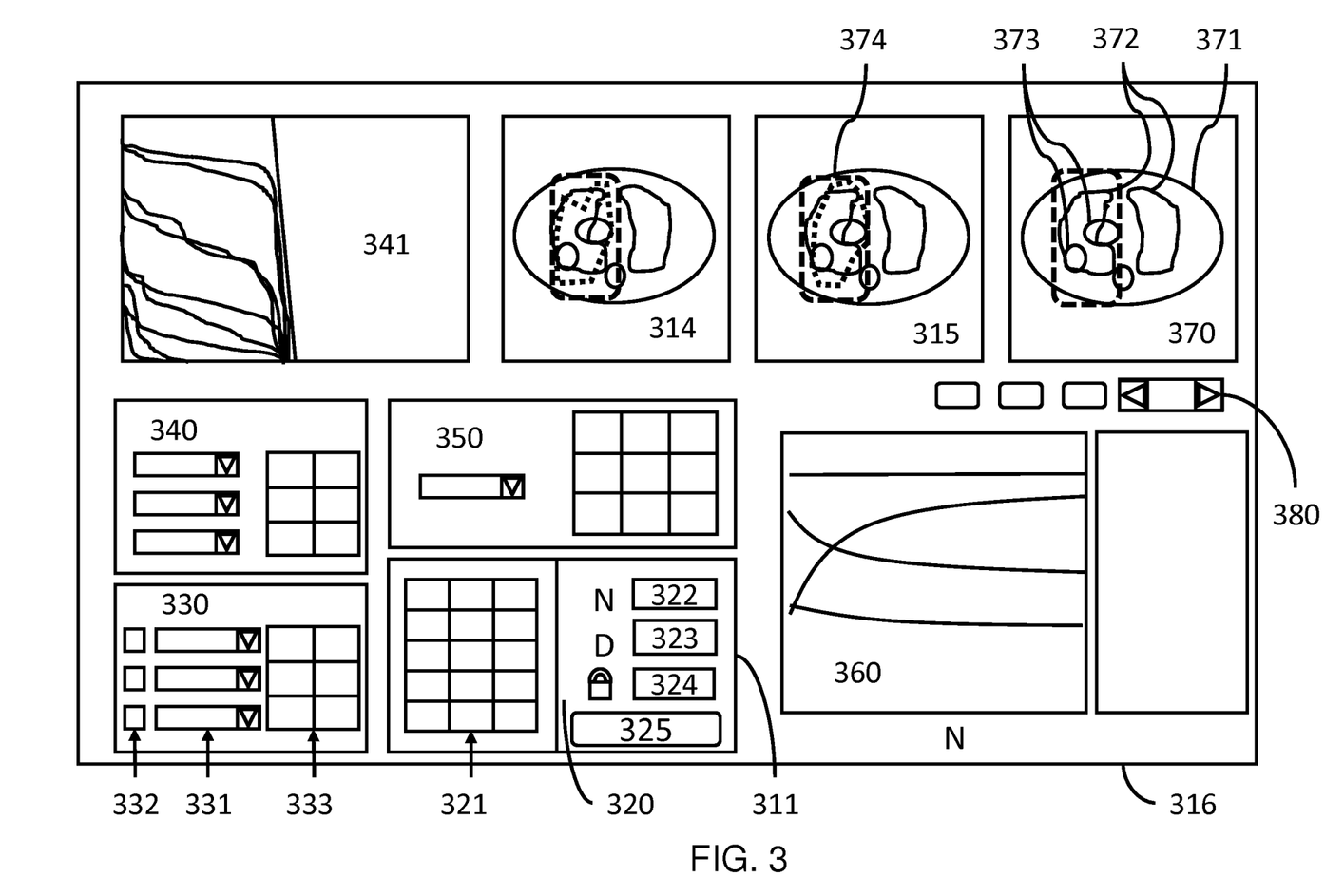
FIG. 3 schematically illustrates an example of a combined graphical output module and fractionation scheme input.

FIG. 3 schematically illustrates an example of a combined graphical output module and fractionation scheme input.

The combined output and input are embodied as a graphical unit interface, or GUI 316. The GUI 316 has a fractionation schemes navigation board 320, an OAR tolerance interface 330, a dose volume histogram viewer 340, a TS information display 350, a biological impact fractionation schemes plot 360, three results displays 314, 315, 370 and a result image slice navigator 380.

The fractionation scheme navigation board 320 comprises the fractionation scheme input 311 for entering a second set of parameters of a fractionation scheme. In this example, the first set of reference parameters of a fractionation scheme are automatically uploaded from a database. However, an additional parameter input for manually entering the reference parameters may also be part of the GUI. The parameter input has entry boxes for entering the number of fractions N 322 and the total dose D 323. The information table 321 in the navigation board 320 provides detailed information on the fractionation schemes. This allows a detailed, numerical comparison of the reference fractionation scheme and the entered second fractionation scheme.

As an additional option, this input 311 also has a checkbox for locking the total biological impact for the TS 324 as a parameter. When the TS biological impact is fixed, the optimal parameters N and D for arriving at this effect can be investigated. The biological impact fractionation schemes plot 360 in this example is a locked target TS plot. The biological impart for the target TS is shown as the straight, fixed line on top. The biological impact on the other TSs and/or OARs is shown as a function of N for the value of D that has been entered. The graph is updated when D is changed. This visualization also assists the physician in his investigation of the optimal fractionation scheme.

Also as an additional option, the input 311 of this embodiment has a maximum TS impact button 325. When this button is activated, the calculation module automatically determines the optimal fractionation scheme fully automatically.

The OAR tolerance interface 330 provides detailed information on the OARs. The OARs of interest may be selected from drop-down menus 331. In this example three options are shown, but more or less options may also be provided. Information on the selected OARs is provided in a table 333. This information may include the total dose received, the total biological impact in the reference fractionation scheme an the total biological impact in the second fractionation scheme. From this information, the physician can determine if the OAR tolerance requirements have been met. He or she can also determine if the received biological impact is well within an acceptable range, or if it is close to the maximum tolerance.

In this embodiment, the OAR tolerance interface also has checkboxes 332 which provide the option of locking an OAR biological impact value. Alternatively numerical inputs could also be provided where the physician can enter the maximum value manually. When one or more of the OAR value locks are used, the maximum biological impact value for the OARs is input into the calculation module as additional parameters of the fractionation scheme. In this way, the OAR tolerance interface 330 may be considered as an addition to the fractionation scheme navigation board 320.

The dose volume histogram viewer 340 is provided for visualizing the current delivered dose at each volume fraction of the OARs and TSs. The OARs and TSs of interest may be selected from drop down menus and information is provided in the form of a table and a graph 341. The information, for example, be the total dose received and biological impact for the first and second fractionation schemes. The graph 341 and table are updated each time the physician enters new values for the fractionation scheme parameters.

The TS information display 350 provides detailed information on the TS. Such information may include the average, minimum and maximum biological impact and/or dose received by the TS. When there is more then one TS, the TS may be selected from a drop-down menu.

The output module of this embodiment shows the results as a set of three pictures 314, 315, 370. The left picture 314 shows the first, reference set of results from the biological impact calculation module, the middle picture 315 shows the second set of results and the right picture 370 shows the difference between the two sets of results.

The results can be presented as pictures in multiple ways, but it will be particularly useful to the physician to include a visualization of the anatomical image data of the subject as well as the calculated biological impact. This can be done in multiple ways, for example by using a gray-scale CT or MRI image of the patient as background. In the current example, the anatomical image data is included as a contour overlay. These contours are preferably the same as the anatomical image data of the subject as used by the calculation module and are the same for all three results pictures. The outer contour in the pictures 371 delineates the patient as a whole. Further contours are included for the OARs 372 and the TSs 373.

The biological impact may also be included in the picture in multiple ways. As one example, the biological impact can be shown as a coloured hot-zone overlay. Such a type of representation is known to the physician, because it is often used for depicting the radiation dose in the radiation therapy planning that precedes the fractionation scheme optimization. This will make the pictures easily understandable and thereby easy in use. An alternative way of depicting the biological impact that is shown in the current example is the use of iso-impact lines. These are lines connecting the point with the same biological impact, dashed lines 374.

Each of the results pictures corresponds to an image slice from the image of the patient. Each slice present a cross-section along the length of the patient. The result image slice navigator 380 allows the physician to navigate through the slices that make up the three-dimensional the image of the relevant part of the patient. The slice navigator in this example has arrows to move from slide to slide and buttons to zoom or pan the image and/or toggle on and off certain parts such as the delineation lines of the anatomical structures.

In the above examples, a system and method for optimizing fractionation schemes in radiation therapy have been described in relation to the planning radiation treatment using a single radiation treatment modality, e.g. photon EBRT, proton or particle EBRT, HDR brachytherapy alone. However, the system and method may equally be applied to optimizing fractionation schemes in the planning of multi-modality radiation therapy. In multi-modality radiation therapy, a treatment consisting of a combination of multiple different radiation treatment modalities is delivered to the patient. Examples from current clinical practice are and initial HDR brachytherapy boost followed by a photon or proton EBRT, or a treatment of combined proton and photon EBRT.

In treatment planning for multi-modality radiation therapy, two pre-optimized dose distributions are provided, a separate one for each treatment. Anatomical data in the form of contours of the OARs and TSs is provided and used for each. Each of the two dose distributions will need to have its own fractionation scheme with corresponding parameters. In the current clinical practice, choices for N and D for each treatment are made separately as if planning were done for a single modality radiation treatment. The choice for the fractionation regime, and in particular the number N, is prescribed based on available clinical guidelines, historical precedence and the physician's judgement based on personal experience. This can already lead to non-optimal choices for each of the modalities separately, which situation is made worse because the non-optimal treatments plans are further combined into the total radiation treatment plan.

The current embodiment addresses this particular additional issue by providing a system and a method for optimizing fractionation schemes in planning radiation therapy, wherein the radiation treatment plan is configured for use in multiple radiation treatment modalities. In this embodiment at least two predetermined radiation therapy plans are received by the input along with anatomical image data of the patient to be treated. The first set of reference parameters of a fractionation scheme now comprises reference parameters for the fractionation schemes for the at least two plans. The fractionation scheme input allows the user to input the second set of reference parameters for the at least two plans. The biological impact calculation module will now calculate the biological impact for each of the treatment modalities for each of the sets of parameters. Advantageously, the calculation module may also calculate the total biological impact of the combined treatment plan for each of the sets of parameters. This allows the physician to assess the biological impact of the fractionation scheme for each of radiation modalities separately as well as the combined total impact for the treatment plan and compare the different options for N and D. In this way the optimal fractionation scheme for the multi-modality radiation therapy plan can be determined.

Figure 4:
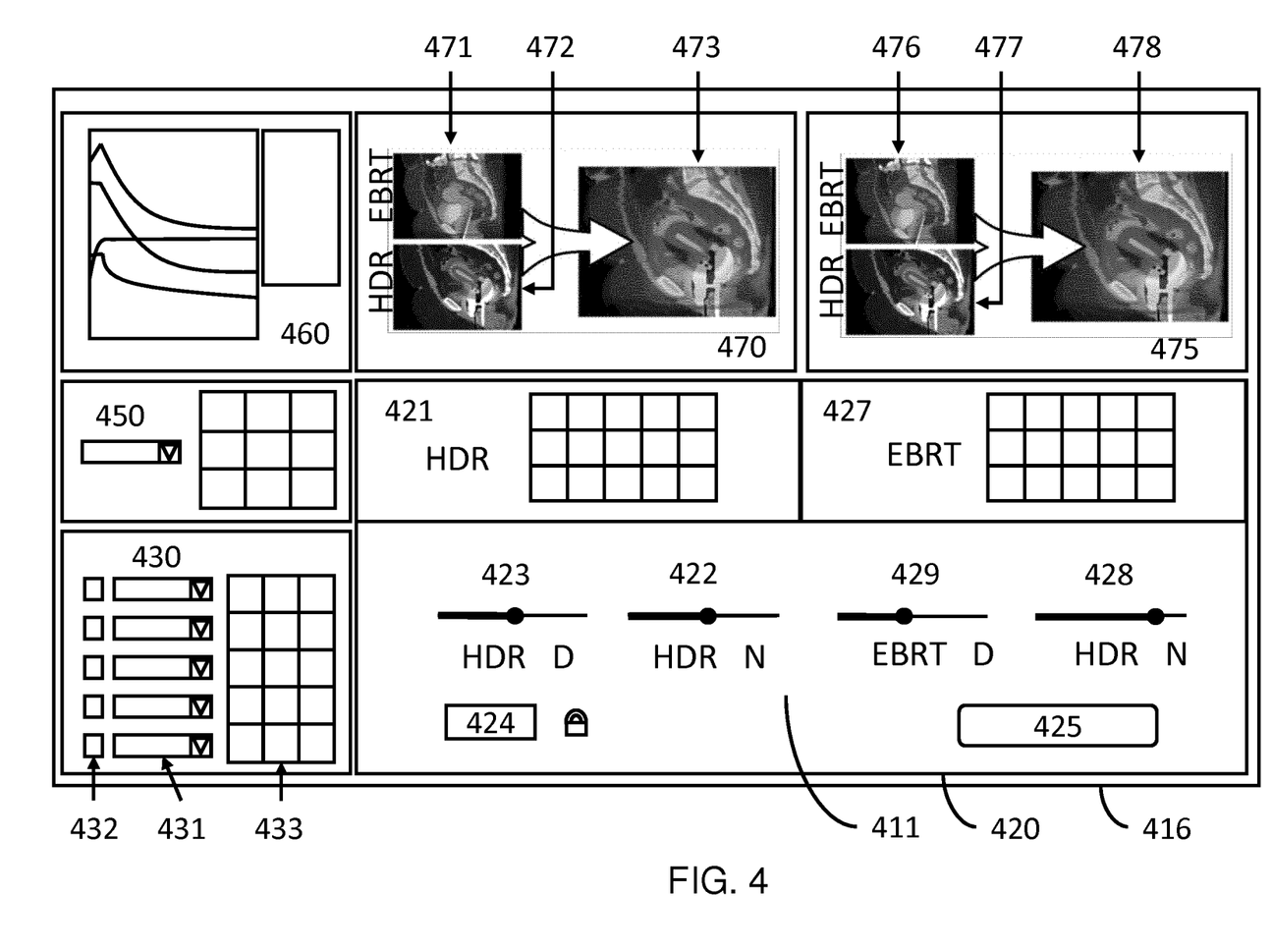
FIG. 4 schematically illustrates an example of a combined graphical output module and fractionation scheme input for use in planning multi-modality radiation therapy.

FIG. 4 schematically illustrates an example of a combined graphical output module and fractionation scheme input for use in optimizing fractionation schemes planning multi-modality radiation therapy. In this example two radiation modalities are used, namely HDR brachytherapy combined with photon EBRT. However, the same concept applies to other combinations of therapies.

The combined output and input are embodied as a graphical unit interface, or GUI 416. The GUI 416 has a fractionation schemes navigation board 420, an OAR tolerance interface 430, a TS information display 450, a biological fractionation schemes plot 460, and two results displays 470, 475.

The fractionation scheme navigation board 420 comprises the fractionation scheme input 411 with controls for entering a second set of parameters of the combined fractionation scheme. In this example, the first set of reference parameters of a fractionation scheme are automatically uploaded from a database. For this multi-modality embodiment, the number of fractions and the total dose is provided for each of the HDR and EBRT modalities separately using sliders. This makes four sliders in total, one for providing the number of HDR fractions 422, one for providing the HDR total dose D 423, one for providing the number of EBRT fractions 428, and one for providing the EBRT total dose D 429. A separate HDR information table 421 in the navigation board 420 provides details on the fractionation scheme for the HDR brachytherapy. Another separate information table 427 in the navigation board 420 provides detailed information on the fractionation scheme for the photon EBRT therapy. This allows a detailed, numerical comparison of the reference fractionation scheme and the second fractionation scheme.

As an additional option, this input 411 also has the checkboxes for locking the combined total biological impact for the TS 424 as a parameter. When the TS biological impact is fixed, the optimal parameters N and D for both types of treatment for arriving at this effect can be investigated. The biological impact fractionation schemes plot 460 is also provided in this example to assists the physician in his investigation of the optimal fractionation scheme.

As a further additional option, the input 411 of this embodiment has a maximum TS impact button 425. When this button is activated, the calculation module iteratively determines the optimal combined fractionation scheme fully automatically. The OAR tolerance interface 430 provides detailed information on the OARs. The OARs of interest may be selected from drop-down menus 431. In this example five options are shown, but more or less options may also be provided. As for the previous embodiment, information on the selected OARs is here also provided in a table 433.

In this embodiment, the OAR tolerance interface also has checkboxes 432 which provide the option of locking an OAR biological impact value. When one or more of the OAR value locks are used, the maximum biological impact value for the OARs is input into the calculation module as additional parameters of the fractionation scheme. In this way, the OAR tolerance interface 430 may be considered as an addition to the fractionation scheme navigation board 420.

The TS information display 450 provides detailed information on the TS. Such information may include the average, minimum and maximum biological impact and/or dose received by the TS. When there is more then one TS, the TS may be selected from a drop-down menu.

The output module of this embodiment shows two display boxes 470, 475 with a set of three pictures each. The left display box 470 shows the first, reference set of results from the biological impact calculation module. The results are presented as a pictures of the biological impact of the photon EBRT 471 and the HDR brachytherapy 472 separately and as a picture of the combined biological impact of both therapies 473. The right display box 475 shows the second set of results. Again the results are presented as a pictures of the biological impact of the photon EBRT 476 and the HDR brachytherapy 477 separately and as a picture of the combined biological impact of both therapies 478. This allows a full visual comparison of the two fractionation schemes for evaluation.

The results can be presented as pictures in multiple ways. In this example, anatomical image data is included by using a gray-scale CT image of the patient as background. The same image is used in all pictures 471, 472, 473, 476, 477, 478. The biological impact may be included in the picture in multiple ways. In this example, the biological impact is a coloured, semi-transparent hot-zone overlay.

Variations to the disclosed embodiments can be understood and effected by those skilled in the art in practicing the claimed invention, from a study of the drawings, the disclosure, and the appended claims. It is noted that the various embodiments may be combined to achieve further advantageous effects.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A system for optimizing fractionation schemes in planning radiation therapy of a subject, the system comprising:
    an input configured to receive anatomical image data of the subject, and a predetermined radiation therapy treatment plan comprising a dose distribution to be delivered to the subject;
    an input configured to receive a first set of reference parameters of a first fractionation scheme;
    a fractionation scheme input configured to receive a second set of reference parameters of a second fractionation scheme;
    a biological impact calculation module stored as instructions in a tangible, non-transitory computer readable medium, wherein the instructions, when executed by a processor, cause the processor to calculate a biological impact of the predetermined radiation therapy treatment plan based on the anatomical image data of the subject, the dose distribution and at least one of the received first and second set of reference parameters; and
    a display configured to simultaneously provide at least two sets of results from the biological impact calculation module, wherein for a first set of results, the first set of reference parameters is used for the calculation of the biological impact, and for a second set of results, the second set of reference parameters is used for the calculation of the biological impact.

2. The system according to claim 1, wherein the display is further configured to provide a difference between the at least two sets of results.

3. The system according to claim 1, wherein the display comprises a graphical display.

4. The system (1) according to claim 1, wherein the fractionation scheme input includes a graphical interface comprising controls for entering the second set of parameters.

5. The system according to claim 1, wherein the display and the fractionation scheme input are provided by a graphical unit interface.

6. The system according to claim 5, wherein the predetermined radiation therapy treatment plan is configured for use in a single radiation treatment modality.

7. The system according to claim 5, wherein the predetermined radiation therapy treatment plan is configured for use in multiple radiation treatment modalities.

8. The system according to claim 1, wherein the system is configured to iteratively receive the second set of reference parameters of the second fractionation scheme such that the calculation of the biological impact is repeated with different values for the second set of reference parameters until the second set of reference parameters corresponding to a maximum biological impact on a region of interest have been determined.

9. An arrangement for planning radiation therapy comprising:
    an imaging device configured to provide an image of a subject to be treated;
    a contouring tool configured to provide anatomical image data based on the image provided by the imaging device;
    a system configured to determine a radiation therapy treatment plan comprising a dose distribution to be delivered to the subject; and
    the system of claim 1 for optimizing the first and second fractionation schemes.

10. The arrangement according to claim 9, wherein the imaging device comprises one or more of a computed tomography (CT) device, magnetic resonance (MR) device, or positron emission tomography (PET) device.

11. A computer-implemented method for optimizing fractionation schemes in planning radiation therapy of a subject, the method comprising:
    receiving anatomical image data of the subject;
    receiving a predetermined radiation therapy treatment plan comprising a dose distribution to be delivered to the subject;
    receiving a first set of reference parameters of a first fractionation scheme;
    receiving a second set of parameters of a second fractionation scheme;
    calculating a biological impact of the predetermined radiation therapy treatment plan based on the anatomical image data, the dose distribution and both the first set and the second set of parameters of the first and second fractionation schemes; and
    providing the calculated biological impact simultaneously for both the first set and the second set of parameters of the first and second fractionation schemes.

12. The method according to claim 11, further comprising calculating a difference between the calculated biological impact for both the first and second set of parameters and providing the calculated difference.

13. The method according to claim 11, further comprising comparing the calculated biological impact for both the first and second set of parameters and evaluating the received first or second sets of parameters to determine which of the first and second fractionation schemes is most suitable for delivery to the subject.

14. The method according to claim 11, wherein the method is performed iteratively using different values for the second set of parameters in each iteration until an optimal set of parameters has been determined.

15. A tangible, non-transitory computer readable medium that stores instructions, which when executed control a processor to perform the method according to claim 11.

\* \* \* \* \*